United States Patent
Benjes et al.

(10) Patent No.: US 7,129,355 B2
(45) Date of Patent: Oct. 31, 2006

(54) PROCESS FOR PREPARING KIFUNENSINE INTERMEDIATE AND KIFUNENSINE THEREFROM

(75) Inventors: Paul Andrew Benjes, Lower Hutt (NZ); Ashley Nicholas Jarvis, London (GB); Gary Brian Evans, Lower Hutt (NZ); Gavin Frank Painter, Lower Hutt (NZ); John Adrian Dickison, Lower Hutt (NZ); Anthony Mitchell, Wellington (NZ); Keith Clinch, Lower Hutt (NZ)

(73) Assignee: Industrial Research Limited (NZ)

( * ) Notice: Subject to any disclaimer, the term of this patent is extended or adjusted under 35 U.S.C. 154(b) by 0 days.

(21) Appl. No.: 10/615,044

(22) Filed: Jul. 8, 2003

(65) Prior Publication Data

US 2004/0063973 A1   Apr. 1, 2004

(30) Foreign Application Priority Data

Jul. 10, 2002   (NZ) ...................... 520108

(51) Int. Cl.
C07D 471/02 (2006.01)
C07D 319/12 (2006.01)
C07D 317/00 (2006.01)

(52) U.S. Cl. ........................ 546/121; 549/377; 549/448

(58) Field of Classification Search ................ 546/121; 549/377, 448
See application file for complete search history.

(56) References Cited

OTHER PUBLICATIONS

Morrison et al., Org. Chem., 3rd edition, (1974), p. 759.*
Elbein et al., *J. Biol. Chem.*, 265 (26), 15599-15605 (Sep. 15, 1990).
Hudlicky et al., *J. Am. Chem. Soc.*, 116, 5099-5107 (1994).
Iwami et al., *Journal of Antibiotics*, 40 (5), 612-622 (May 1987).

Kayakiri et al., *J. Org. Chem.*, 54, 4015-4016 (1989).
Kayakiri et al., *Tetrahedrom Lett.*, 31 (2), 225-226 (1990).
Kayakiri et al., *Chem. Pharm. Bull.*, 39 (6), 1378-1381 (1991).
Kayakiri et al., *Chem. Pharm. Bull.*, 39 (6), 1392-1396 (1991).
Rouden et al., *J. Chem. Soc. Perkin Trans.*, 1, 1095-1097 (1993).

* cited by examiner

Primary Examiner—Taofiq Solola
(74) Attorney, Agent, or Firm—Leydig, Voit & Mayer, Ltd.

(57) ABSTRACT

A novel method for the preparation of a compound of formula (I) from an N—protected-D-mannosamine. A compound of formula (I) is a useful intermediate for the preparation of kiftnensine, a potent and selective mannosidase inhibitor. The method includes protecting the hydroxyl group at the C-6 position of an N—protected-D-mannosamine, to give a 6—O—protected—N—protected-D-mannosamine; reducing the C-1 anomeric carbon atom of the 6—O—protected—N—protected-D-mannosamine to give a 6—O—protected—N—protected-D-mannitol; protecting the four hydroxyl groups of the 6—O—protected—N—protected-D-mannitol; and removing the nitrogen atom protecting group and optionally removing the C-6 oxygen atom protecting group to give the compound of formula (I):

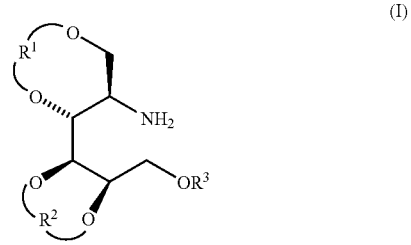

(I)

where $R^1$ and $R^2$ are each independently protecting groups which, together with the oxygen atoms to which they are attached, form a 5-, 6-, 7- or 8-membered ring; and $R^3$ is hydrogen or a protecting group.

16 Claims, No Drawings

PROCESS FOR PREPARING KIFUNENSINE INTERMEDIATE AND KIFUNENSINE THEREFROM

This invention relates to a novel method for the preparation of an intermediate useful for preparing kifunensine. The invention also relates to a method of preparing kiftnensine

BACKGROUND

Kifunensine was first isolated from the actinomycete *Kitasatosporia kifunense* No. 9482 in 1987 (M. Iwami, O. Nakayama. H. Terano, M. Kohsaka, H. Aoki and H. Imanaka, *J. Antibiot.*, 40, 612, 1987) and is a cyclic oxamide derivative of 1-amino-mannojirimycin. Its basic framework combines aspects of oxygenated indolizidine alkaloids with those of the aza sugars.

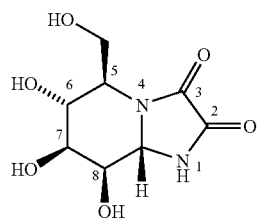

Kifunensine

Kiftnensine is a selective and potent mannosidase inhibitor. It is a very effective inhibitor of the plant glycoprotein processing enzyme mannosidase I (an $IC_{50}$ of about 2–5× $10^{-8}$ M was observed against the purified enzyme), but is inactive toward plant mannosidase II (A. D. Elbein, J. E. Tropea, M. Mitchell, and G. P. Kaushal, *J. Biol. Chem.*, 265, 15599, 1990). Kifunensine has also shown promising immunomodulatory activity in α-mannosidase inhibition.

The synthesis of kiflinensine has been reported by both Fujisawa Pharmaceutical Co. (H. Kayakiri, C. Kasahara, T. Oku, and M. Hashimoto, *Tetrahedron Lett.*, 31, 225, 1990, H. Kayakiri, C. Kasahara, K. Nakamura, T. Oku, and M. Hashimoto, *Chem. Pharm. Bull.*, 39, 1392, 1991) and Hudlicky et al. (J. Rouden and T. Hudlicky, *J. Chem. Soc. Perkin Trans.* 1, 1095, 1993; J. Rouden, T. Hudlicky, H. Luna and S. Allen, *J. Am. Chem. Soc.*, 116, 5099, 1994).

The Fujisawa route produces kifunensine in 8 synthetic steps from mannosamine hydrochloride, which already possesses much of the desired stereochemistry. The process involves the interchange of the C-1 aldehyde and C-6 hydroxymethyl groups of D-mannosamine. The key step is a double cyclisation of an oxamide-aldehyde precursor with ammonia. An overall yield of 33% was reported. It has been found by the applicant that the Fujisawa route does not respond well to scale up and is prone to marked irreproducibility in the silylation step, resulting in a lower overall yield than that reported.

Hudlicky et al. have synthesised kifunesine in a 13 step process starting from achiral chlorobenzene. Chirality is introduced early via a microbial dihydroxylation using Pseudomonas putida 39D. The Hudlicky route involves a microbial oxidation which introduces many complications on scale up. This route also involves the use of hazardous reagents such as sodium azide, mCPBA and ozone.

The applicant has now found that kifunensine may be synthesised from N—acetyl-D-mannosamine, in a manner which avoids, at least in part, some of the abovementioned problems.

It is therefore an object of this invention to provide a novel method of preparing an intermediate[PB1] for the preparation of kifinensine. It is also an object of the invention to provide a method of preparing kifunensine from this intermediate. These objects of the invention are to be read with the alternative object of at least providing the public with a useful choice.

STATEMENTS OF INVENTION

In one aspect, the invention provides a process for preparing a compound of formula (I), or a salt thereof:

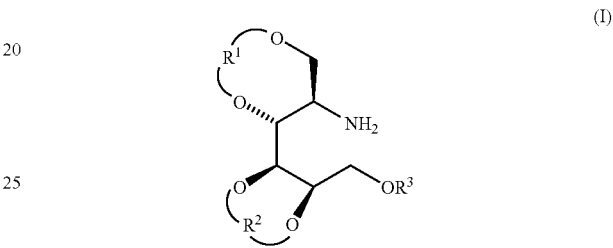

where R1 and R2 are each independently protecting groups which, together with the oxygen atoms to which they are attached, form a 5-, 6-, 7- or 8-membered ring; and R3 is hydrogen or a protecting group; including the steps of:

(a) protecting the hydroxyl group at the C-6 position of an N—protected-D-mannosamine, to give a 6—O—protected—N—protected-D-mannosamine;

(b) reducing the C-1 anomeric carbon atom of the 6—O—protected—N—protected-D-mannosamine to give a 6—O—protected—N—protected-D-mannitol;

(c) protecting the four hydroxyl groups of the 6—O—protected—N—protected-D-mannitol; and (d) removing the nitrogen atom protecting group and optionally removing the C-6 oxygen atom protecting group to give the compound of formula (I).

Preferably the N—protected-D-mannosamine is an N—acyl-D-mannosamine. More preferably the N—protected-D-mannosamine is N—acetyl-D-mannosamine.

Preferably R1 and R2, together with the oxygen atoms to which they are attached, each independently form part of a dioxane or a dioxolane ring. More preferably R1 and R2 are both isopropylidene protecting groups.

Preferably the hydroxyl group at the C-6 position of the N—protected-D-mannosamine in step (a) is protected using a silylating agent. More preferably the silylating agent is tert-butyldiphenylsilyl chloride, so that R3 is a tert-butyldiphenylsilyl group.

Preferably the C-1 anomeric carbon atom of the 6—O—protected—N—protected-D-mannosamine is reduced in step (b) above using a metal hydride reducing agent such as sodium borohydride. Alternatively, it is preferred that the C-1 anomeric carbon atom is reduced by hydrogenation using hydrogen gas and a metal catalyst. [PB2]

Preferably 2,2-dimethoxypropane in the presence of acetone is used to protect the four hydroxyl groups of the 6—O—protected—N—protected-D-mannitol in step (c) above, to give a 1:3,4:5-di—O—isopropylidene-D-mannitol.

Preferably both the nitrogen atom protecting group and the C-6 oxygen atom protecting group are removed in step (d) above. More preferably both the nitrogen atom protecting group and the C-6 oxygen atom protecting group are removed using an aqueous barium hydroxide solution.

In a preferred embodiment of the invention, the process further includes the preparation of kifunensine from the compound of formula (I) as defined above.

Preferably the preparation of kifunensine from the compound of formula (I) includes the steps of:
- (e) oxamoylation of the compound of formula (I) to give a 2-oxamoylamino-D-mannitol;
- (f) removal of the R3 protecting group (if R3 is not H);
- (g) oxidation of the C-6 carbon atom to give a 5-oxamoylamino-D-mannose;
- (h) double cyclisation of the 5-oxamoylamino-D-mannose to give kifimensine with four protected hydroxyl groups; and
- (i) removal of the four hydroxyl protecting groups to give kifunensine.

Preferably the removal of the R3 protecting group is carried out after the oxamoylation step. More preferably the removal of the R3 protecting group is carried out after the oxamoylation step and before the oxidation step.

It is preferable that the R3 protecting group is removed using an aqueous barium hydroxide solution. It is also preferable that the R3 protecting group is removed using sodium n-butoxide in n-butanol.

It is preferred that oxamic acid and 1,1'-carbonyldiimidazole are used for the oxamoylation of the compound of formula (I) in step (e). Alternatively, it is preferred that the oxamoylation is a direct coupling of the compound of formula (I) with ethyl oxamate, oxalic acid mono-n-butyl ester or di-n-butyl oxalate.

Any suitable oxidising agent may be used for the oxidation of the C-6 carbon atom in step (g). However, pyridinium dichromate in the presence of activated molecular sieves and pyridinium trifluoroacetate is preferred. Other oxidising agents that may be used include Dess-Martin periodinane, 2,2,6,6-tetramethyl-1-piperidinyloxy/trichloroisocyanuric acid, tetrapropylammonium perruthenate/4-methylmorpholine N—oxide, ruthenium (III) chloride/sodium periodate and trifluoroacetic anhydride/dimethylsulfoxide.

Preferably ammonia in methanol is used in the double cyclisation in step (h).

It is preferred that the four hydroxyl protecting groups are removed using methanolic hydrochloric acid. Alternatively, the four protecting groups may be removed using trifluoroacetic acid.

In a preferred embodiment of the invention, the preparation of kifunensine includes the steps:
- (a) silylation of N—acetyl-D-mannosamine using tert-butyldiphenylsilyl chloride as silylating agent, to give 6—O—tert-butyldiphenylsilyl-2-deoxy-2-acetylamino-D-mannose;
- (b) reduction of 6—O—tert-butyldiphenylsilyl-2-deoxy-2-acetylamino-D-mannose using sodium borohydride as reducing agent, to give 6—O—tert-butyldiphenylsilyl-2-deoxy-2-acetylamino-D-mannitol;
- (c) protection of the four hydroxy groups of 6—O—tert-butyldiphenylsilyl-2-deoxy-2-acetylamino-D-mannitol using 2,2-dimethoxypropane in the presence of acetone, to give 6—O—tert-butyldiphenylsilyl-2-deoxy-1,3:4,5-di—O—isopropylidene-2-acetylamino-D-mannitol;
- (d) double deprotection of the 6—O—and N—protecting groups of 6—O—tert-butyldiphenylsilyl-2-deoxy-1,3:4,5-di—O—isopropylidene-2-acetylamino-D-mannitol using aqueous barium hydroxide, to give 2-amino-2-deoxy-1,3:4,5-di—O—isopropylidene-D-mannitol;
- (e) oxamoylation of 2-amino-2-deoxy-1,3:4,5-di—O—isopropylidene-D-mannitol using oxamic acid and 1,1'-carbonyldiimidazole, to give 2-deoxy-1,3:4,5-di—O—isopropylidene -2-oxamoylamino-D-mannitol;
- (f) oxidation of 2-deoxy-1,3:4,5-di—O—isopropylidene-2-oxamoylamino-D-mannitol using pyridinium dichromate in the presence of activated molecular sieves and pyridinium trifluoroacetate, to give 5-deoxy-2,3:4,6-di—O—isopropylidene-5-oxamoylamino-D-mannose;
- (g) double cyclisation of 5-deoxy-2,3:4,6-di—O—isopropylidene-5-oxamoylamino-D-mannose using a methanolic ammonia solution, to give 2,3:4,6-di—O—isopropylidene-kifunensine; and
- (h) deprotection of 2,3:4,6-di—O—isopropylidene-kifunensine, using methanolic hydrochloric acid, to give kifunensine.

In another aspect, the invention provides the use of a compound of formula (I) in the preparation of kifunensine.

DETAILED DESCRIPTION

It is to be understood that the term "protecting group" as used herein means "a group that selectively protects an organic functional group, temporarily masking the chemistry of that functional group and allowing other sites in the molecule to be manipulated without affecting the functional group".

The protecting group strategy for the process of this invention requires the protection of three types of functional groups, namely a nitrogen, a primary hydroxyl group, and four secondary hydroxyl groups.

Protecting groups should be chosen for:
1. the nitrogen, such that the protecting group is stable under the reaction conditions for protection of the primary and secondary hydroxyl groups;
2. the primary hydroxyl group, such that the protecting group is stable under the reaction conditions for protection of the secondary hydroxyl groups;
3. the secondary hydroxyl groups, such that the protecting group is stable under the reaction conditions for deprotection of the nitrogen and the primary hydroxyl group.

Examples of primary hydroxyl protecting groups include silyl protecting groups such as tert-butyldiphenylsilyl. Additional examples include (substituted) benzyl groups and ester groups.

The use of cyclic protecting groups to protect the secondary hydroxyl groups is particularly desirable in the process of the invention. For example, isopropylidene groups may be employed, resulting in the formation of dioxanes or dioxolanes.

Examples of nitrogen protecting groups include acyl groups such as the acetyl group. The nitrogen may also be protected as the carbamate. Additional examples of nitrogen protecting groups include sulfonyl groups. The nitrogen may also be protected as an azido group.

The process of the invention is based on the applicant's synthesis of kifunensine, which involves the conversion of N—acetyl-D-mannosamine (1) into 2-amino-2-deoxy-1,3:4,5-di—O—isopropylidene-D-mannitol, (5) (Scheme 1). The remaining steps to convert compound (5) to kifunensine are a variation on the Hudlicky/Fujisawa routes. The following detailed description depicts the synthetic route to kifunensine developed by the applicant. This route is only one example of the invention. It is to be appreciated that the invention is not intended to be limited to this example.

Scheme 1

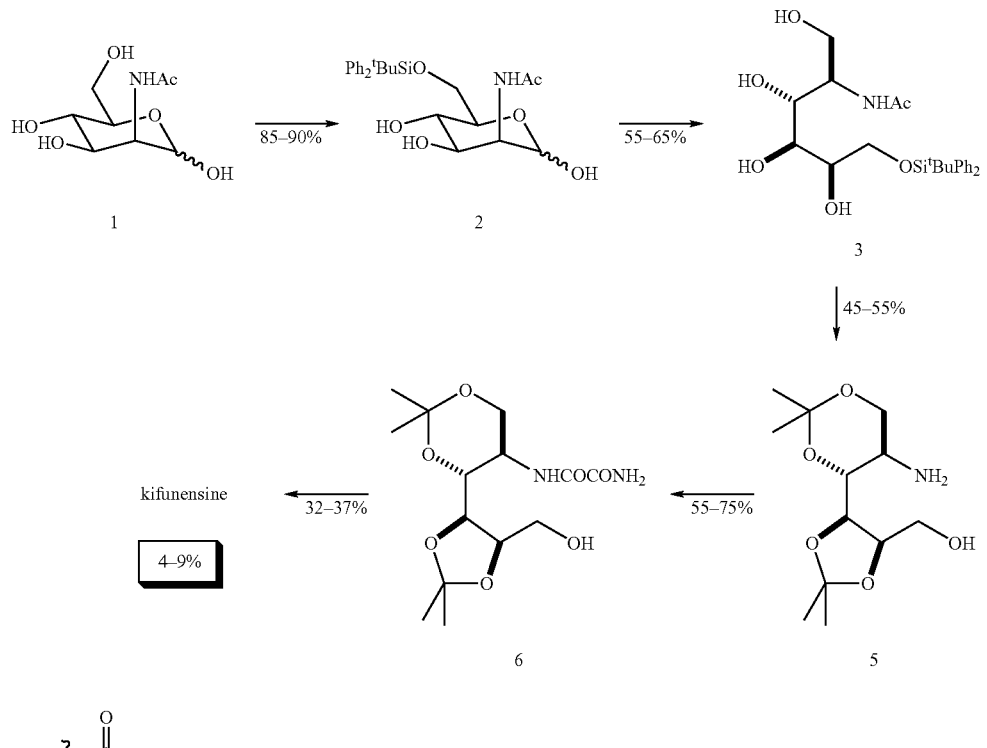

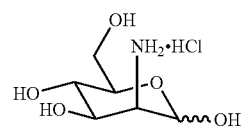

N—Acetyl-D-mannosamine, (1) (Scheme 2) is the starting material for the new route to kifunensine. Compound (1) can be prepared from N—acetyl-D-glucosamine in approximately 10% yield by base-catalyzed epimerisation. The synthesis of D-mannosamine hydrochloride (Scheme 2) affords (1) as an intermediate in pure (crystalline) form by selective extraction/crystallization of the neutralized and lyophilized epimerization mixture.

Scheme 2

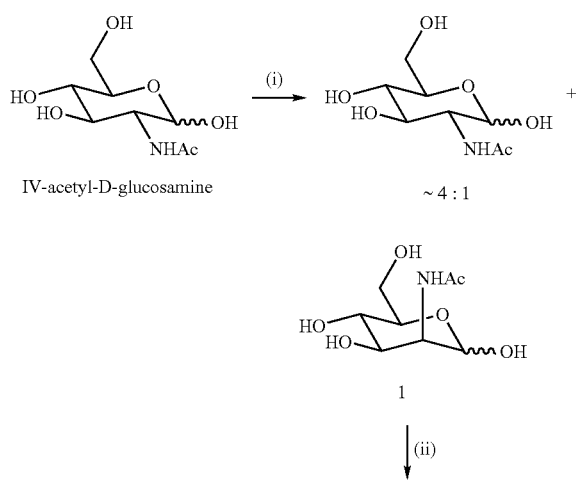

-continued

D-mannosamine•HCl (i) 20% Ca(OH)$_2$/H$_2$O, <20° C.; (ii) aq. HCl/reflux

The silylation of (1) with tert-butyldiphenylsilyl chloride (TBDPSCl) (Scheme 3) reproducibly affords the mono-6—O—silylated product (2) in very high yield (greater than 85% yield after chromatography). A reaction carried out on a 50 g scale exhibits identical behaviour to sub-gram scale reactions, demonstrating the ease of scale-up of the procedure. The ratio of mono-6—O— to 1,6-di—O—silylated products (2):(10) is consistently of the order of 9:1.

Because the starting material (1) is isolated as a hydrate, prior removal of the water of crystallization by co-evaporation with N,N—dimethylformamide (DMF) is necessary to keep to a minimum the amount of TBDPSCl required to perform the conversion.

Purification is not necessary at this point as the di-silylated by-product can be removed chromatographically, unchanged, after the reduction step (ii).

Scheme 3

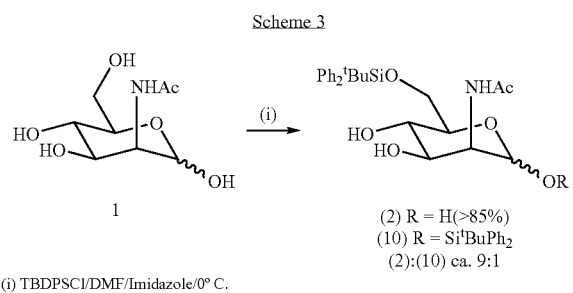

(2) R = H (>85%)
(10) R = Si<sup>t</sup>BuPh<sub>2</sub>
(2):(10) ca. 9:1

(i) TBDPSCl/DMF/Imidazole/0° C.

The reduction of mannose derivative (2) to mannitol (3) is achieved by the use of sodium borohydride in methanol (Scheme 4). The reaction proceeds cleanly, as monitored by thin layer chromatography (TLC), and the yield is typically greater than 70%. The work-up involves ethyl acetate extraction of the product from a mildly acidic (pH 6) aqueous solution and analysis of this aqueous layer does not reveal any O-desilylated or N—deacetylated degradative material. Chromatography is used to isolate the mannitol (3). Elution and concomitant quench of the reduction mixture through an Amberjet acid resin may also be used. The yield is similar but the product is isolated in a cruder state.

Scheme 4

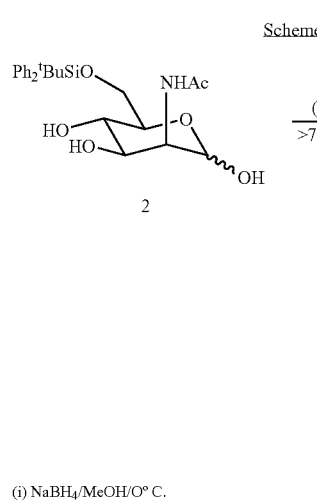

(i) NaBH<sub>4</sub>/MeOH/0° C.

Hydrogenation of (2) is an alternative to the use of sodium borohydride. Using Raney Nickel catalyst (NDHT-MO, a sponge Nickel catalyst, Kawaken Fine Chemicals), 50 bar pressure and a reaction temperature of 85° C. for 7 hours, mannitol (3) is produced quite cleanly and simply. At temperatures below 85° C. the rate of reaction is prohibitively slow (e.g. reaction time of 25 hours at 75° C.) and at temperatures above 85° C. (e.g. reaction times of 6 hours at 100° C.) degradation/by-products become more apparent in the product mixture.

Diacetonide (4) is formed from (3) using catalytic para-toluenesulfonic acid monohydrate (PTSA) in the presence of acetone and 2,2-dimethoxypropane (DMP) (Scheme 5). PTSA was found to be a better catalyst than camphorsulfonic acid (CSA). Using PTSA, higher reaction temperatures are unnecessary and the reaction is complete within 5 hours at 20° C. After filtration through a plug of silica, diacetonide (4) can be crystallized from light petroleum ether in yields typically greater than 60% yield.

Scheme 5

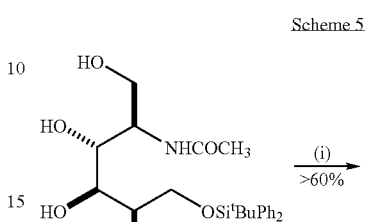

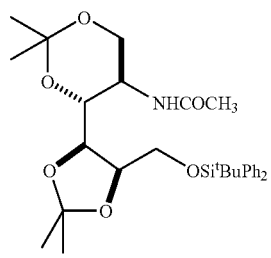

(i) Me<sub>2</sub>CO/2, 2-dimethoxypropane/PTSA/20° C.

The removal of the O-tert-butyldiphenylsilyl and N—acetyl groups from (4) can be accomplished concomitantly by treatment with an aqueous barium hydroxide solution at high temperature and elevated pressure (Scheme 6). A good yield of 80% of the amino-alcohol (5) is obtained after chromatographic purification.

To solubilize the reagent and starting material (4), a 2:1 water/dioxane solvent system is used. Temperatures in the range 130–140° C. are necessary to produce an acceptable reaction rate. Even at these temperatures, an 18 hour reaction time is required, as is the use of a pressure rated reaction vessel. Calorimetric experiments have determined that a pressure of 6 bar is generated under these conditions, and hence that an 8 bar rated reaction vessel is adequate to these needs.

Other alternative methods include treatment of (4) with sodium n-butoxide in n-butanol at atmospheric reflux. However, the reaction does not proceed as cleanly. Thus, despite the need for a pressure vessel, the barium hydroxide reaction is still favoured. From a large scale standpoint, a move away from 1,4-dioxane as a reaction solvent is desirable, and the use of a methanol/water mixture may be employed. The reaction is still successful under these conditions, though there is a drop in yield and the generation of higher reaction pressures necessitates the use of a lower reaction temperature and a longer reaction time.

Scheme 6

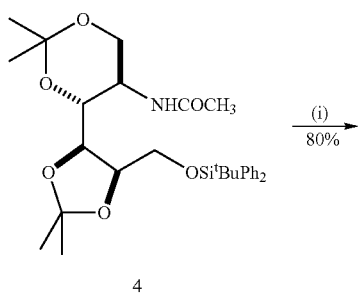

4

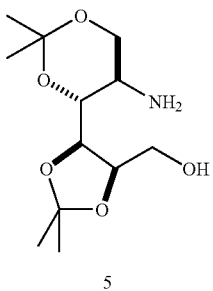

5

(i) 4 eq. Ba(OH)$_2$/Dioxane: H$_2$O (1:2)/130–140° C./sealed tube

The oxamoylation of the amino group of (5) produces intermediate (6) (Scheme 7, (a)). Treatment of (5) with oxamic acid under standard coupling conditions affords (6) relatively cleanly by TLC. However, the generation of the active acylating agent (by prior treatment of oxamic acid with 1,1'-carbonydiimidazole (CDI)) is non-trivial and purification is greatly complicated by the fact that (6) is soluble in both organic and aqueous media and thus cannot be subjected to an extractive work-up procedure. Chromatography is the only purification option available to separate (6) from imidazole, a by-product in the reaction. Unavoidable traces of the DMF reaction solvent complicate this purification still further.

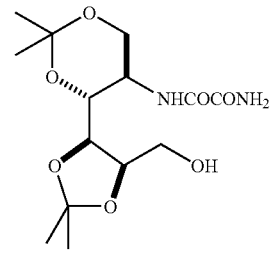

6

(a) CDI/oxamic acid/DMF/20° C.; or (b) ethyl oxamate/EtOH/125° C./sealed tube

Alternative coupling reactions may be employed. The direct coupling of (5) with ethyl oxamate (Scheme 7, (b)) proceeds in ethanol under sealed tube conditions. However, by-products are apparent in the product mixture and separation of these and unreacted ethyl oxamate from (6) is also non-trivial.

Alternatively, the coupling of (5) with oxalic acid mono-n-butyl ester makes the coupled product more lipophilic and amenable to an extractive work-up (Scheme 8, (a)). Treatment of the acid derivative with CDI produces an active ester that readily couples with (5) to produce (11) as the major product. Imidazole by-product is readily separated by partitioning the mixture between an organic solvent and an aqueous acid solution. Subsequent treatment of (11) with methanolic ammonia results in ammonolysis and the formation of (6), cleanly and in good overall yield (60–73%, 2 steps). The material from this process does not need chromatographic purification before proceeding to the oxidation step.

The coupling of (5) with di-n-butyl oxalate to give (11) (Scheme 8, (b)) avoids the need for CDI and appears to proceed cleanly, but is difficult to drive to completion at 80–90° C. The use of higher temperatures results in the formation of substantial by-products. Again, treatment of (11) with methanolic ammonia results in ammonolysis and the formation of (6).

Scheme 7

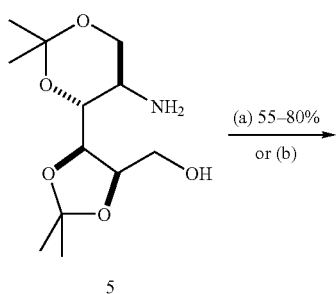

5

(a) 55–80% or (b)

Scheme 8

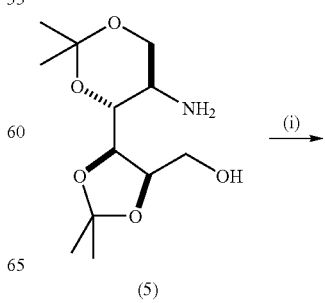

(5)

-continued

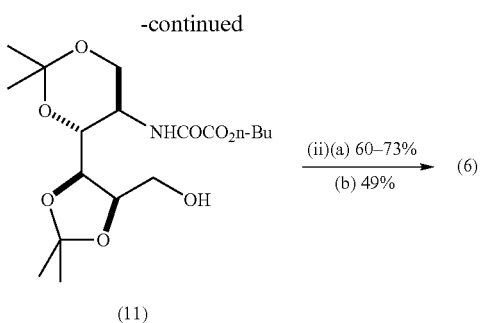

(a)(i) oxalic acid mono-n-butyl ester/CDI/DMF/20° C., (ii) 7N NH₃ in MeOH/20° C.; or (b) di-n-butyl oxalate/n-BuOH/85° C., (ii) 7N NH₃ in MeOH/20° C.

The oxidation step uses the mild oxidant pyridinium dichromate (PDC) in conjunction with activated powdered molecular sieves (4 Å) and 40 mol % pyridinium trifluoroacetate. Complete oxidation of (6), to the desired aldehyde, is observed, as monitored by TLC, after 30 minutes. This method has the dual advantage of requiring merely stoichiometric amounts of oxidant, coupled with a greatly simplified work-up, in terms of processing ease.

In contrast, the published oxidation procedure uses Collins reagent (dipyridine chromium(VI) oxide), requiring the use of a large excess of the toxic oxidant. Alternative oxidants have been trialled, such as Dess-Martin Periodinane, 2,2,6,6-tetramethyl-1-piperidinyloxy (TEMPO)/trichloroisocyanuric acid, tetrapropylammonium perruthenate (TPAP)/4-methylmorpholine N—oxide (NMO), ruthenium (III) chloride/sodium periodate and trifluoroacetic anhydride (TFAA)/dimethylsulfoxide (DMSO).

Treatment of the aldehyde oxidation product with a solution of ammonia in methanol results in a double cyclisation to produce protected kifunensine, (8). The use of isopropylidene protecting groups is convenient as the intermediates (4) and (5) are crystalline and, importantly, these groups promote cyclisation in favour of (8) as opposed to the C-8a epimer (epi-kifunensine).

Scheme 9

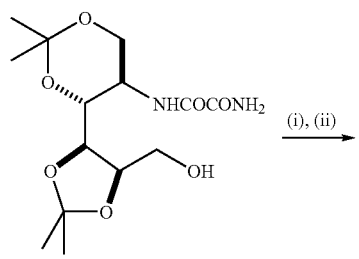

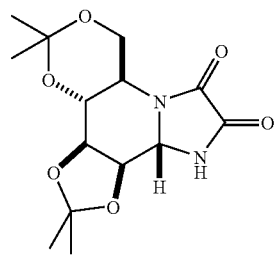

(i) PDC/CH₂Cl₂/4A mol. sieves/pyridine/trifluoroacetic acid; (ii) 7N NH₃ in MeOH The final deprotection step uses methanolic hydrochloric acid (Scheme 10). Kifunensine precipitates from the reaction mixture and can be isolated by simple filtration. A final recrystallisation from water is necessary to remove trace inorganic contaminants.

Alternatively, trifluoroacetic acid may be employed in the deprotection step.

The final 3 steps are carried out without chromatographic purification and observed yields are typically in the range 33–37% [prior to recrystallization and based on oxamidoalcohol (6)].

Scheme 10

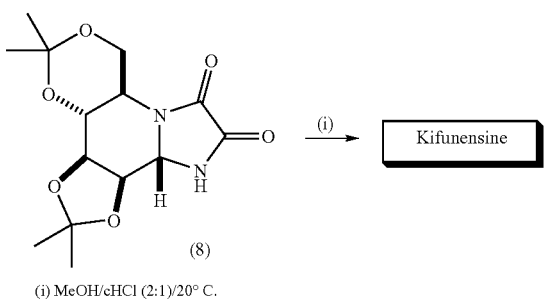

(i) MeOH/cHCl (2:1)/20° C.

The overall yield for the process is 4–9%. The new synthetic route has advantages over the Fujisawa and Hudlicky routes. In particular, the silylation step is both scaleable and reproducible. Furthermore, the new route has much greater processing ease, including simpler chromatographic operations and reaction work-ups. The use of a microbial oxidation is avoided, as is the use of the hazardous reagents employed in the Hudlicky method.

EXAMPLES

The invention is further described with reference to the following examples. It is to be appreciated that the invention is not limited by these examples.

Example 1

Preparation of 6—O—tert-butyldiphenylsilyl-2-deoxy-2-acetylamino-D-mannose

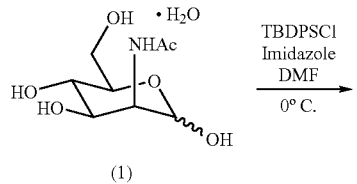

(1)
C₈H₁₅NO₆·H₂O
Mol. Wt.: 239.23
C, 40.17; H, 7.16; N, 5.86; O, 46.82

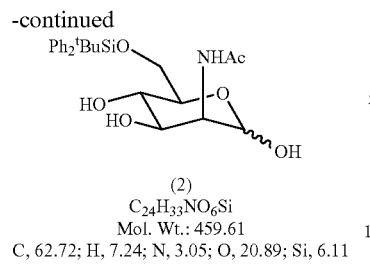

(2)
C24H33NO6Si
Mol. Wt.: 459.61
C, 62.72; H, 7.24; N, 3.05; O, 20.89; Si, 6.11

N—Acetyl-D-mannosamine (1) (50.7g, 0.21 mol) was dissolved in 500 mL of anhydrous N,N—dimethylformamide and the mixture was concentrated to dryness. This was repeated and the resulting residue was then redissolved in 400 mL of anhydrous N,N—dimethylformamide and placed under an inert atmosphere. Imidazole (21.3 g, 0.31 mol) was added as a single portion and the solution cooled to 0° C. tert-Butyldiphenylsilyl chloride (67 g, 0.24 mol), in 100ml of anhydrous N,N—dimethylformamide, was added dropwise, at 0° C., over 2.5 hour and the mixture left to stir for a further 30 min. A further portion of tert-butyldiphenylsilyl chloride (2.9 g, 0.01 mol) was added dropwise and the mixture left to stir for a further 30 min at 0° C. The reaction was quenched by the addition of 100 mL of water. The mixture was partitioned between 1500 mL of water and 750 mL of ethyl acetate and the aqueous layer then extracted twice more with 750 mL portions of ethyl acetate. The combined organic layers were washed three times with 300 mL of saturated, aqueous sodium chloride solution, dried over magnesium sulfate and concentrated under reduced pressure to afford approx. 133 g of a colourless viscous syrup. This oil was subjected to dry-flash chromatography affording (2) [90 g, 92%] as a colourless foam. Mp 77–79° C. $^1$H NMR (300 MHz, DMSO-$d_6$-$D_2$O) δ: 7.69–7.66 (4H, m), 7.49–7.40 (6H, m), 4.94 (0.7H, br s), 4.75 (0.3H, br s), 4.17–3.17 (6H, m), 1.88 (3H, br s), 1.01 (9H, s). $^{13}$C NMR (300 MHz, DMSO-$d_6$) δ: 170.1, 135.6, 135.5, 133.9, 133.7, 130.0, 128.1, 92.9, 73.5, 72.9, 68.6, 67.5, 54.4, 27.1, 23.1, 19.3.

It should be noted that the crude material, prior to chromatography, is suitable for use in the subsequent reduction step.

Example 2

Preparation of 6—O—tert-butyldiphenylsilyl-2-deoxy-2-acetylamino-D-mannitol

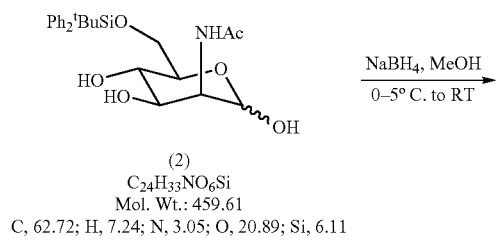

(2)
C24H33NO6Si
Mol. Wt.: 459.61
C, 62.72; H, 7.24; N, 3.05; O, 20.89; Si, 6.11

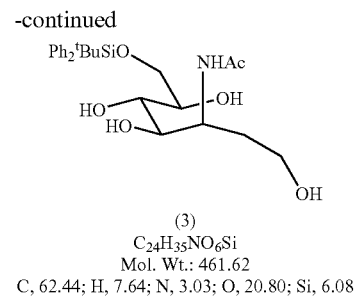

(3)
C24H35NO6Si
Mol. Wt.: 461.62
C, 62.44; H, 7.64; N, 3.03; O, 20.80; Si, 6.08

The monosilylated material (2) (90 g, 0.20 mol) was dissolved in 1 L of distilled methanol and the solution cooled to 0° C. under an inert atmosphere. Sodium borohydride (36 g, 0.98 mol) was added portionwise over 1.5 hour at 0–5° C. The mixture was allowed to warm to room temperature with stirring over 16 hours. The majority of the methanol (approx. 700 mL) was removed under reduced pressure and the resulting grey suspension was diluted with water (250 mL). Hydrochloric acid (1 M; 190 mL) was added dropwise at room temperature to provide a white suspension. Ethyl acetate (500 mL) was added and the suspension stirred for 30 minutes to provide homogeneous aqueous and organic phases. The aqueous layer was separated and further extracted with 2×500 mL of ethyl acetate. The organic layers were combined and washed with saturated, aqueous sodium bicarbonate (300 mL) and saturated, aqueous sodium chloride (300 mL), dried over magnesium sulfate and concentrated under reduced pressure to afford the crude product as a colourless foam (79 g). The foam was subjected to dry-flash chromatography to provide (3) (65 g, 72%) as a colourless foam. $R_f$ 0.51 (methanol/ethyl acetate, 0.5:9.5). $^1$H NMR (300 MHz, DMSO-$d_6$) δ: 7.76 (1H, d, J=7.9 Hz), 7.69–7.66 (4H, m), 7.45–7.39 (6H, m), 4.63–4.57 (2H, m), 4.39 (1H, d, J=5.2), 4.27 (1H, d, J=7.6), 3.85–3.58 (7H, m), 3.43–3.38 (1H, m), 1.85 (3H, s), 0.99 (9H, s). $^{13}$C NMR (300 MHz, DMSO-$d_6$) δ: 171.2, 135.6, 135.5, 133.9, 133.8, 130.0, 128.1, 70.9, 69.5, 68.6, 66.7, 61.1, 53.4, 27.0, 22.9, 19.3.

Example 3

Preparation of 6—O—tert-butyldiphenylsilyl-2-deoxy-2-acetylamino-D-mannitol

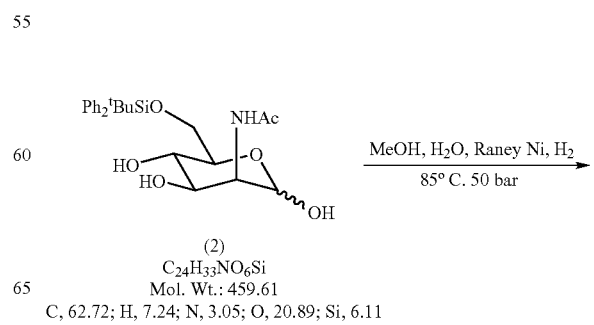

(2)
C24H33NO6Si
Mol. Wt.: 459.61
C, 62.72; H, 7.24; N, 3.05; O, 20.89; Si, 6.11

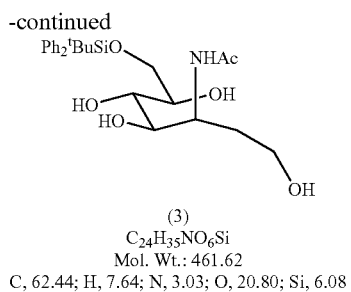

(3)
C$_{24}$H$_{35}$NO$_6$Si
Mol. Wt.: 461.62
C, 62.44; H, 7.64; N, 3.03; O, 20.80; Si, 6.08

The monosilylated material (2) (2 g, 4.4 mmol) was dissolved in 25 mL of distilled methanol and 25 mL of distilled water and the solution placed in the 'bomb' hydrogenation apparatus. Raney Nickel (NDHT-MO, 0.25 g) was further added and the resulting suspension agitated at 85° C., under hydrogen (50 bar), for 7 hours. The reaction mixture was cooled to room temperature, filtered through Celite and the filter cake washed with methanol (2×15 mL). The solvent was removed under reduced pressure to afford a colourless foam (2 g, quantitative). The data obtained corresponded to that observed for the synthesis of (3) depicted in Example 2.

Example 4

Preparation of 6—O—tert-butyldiphenylsilyl-2-deoxy-1,3:4,5-DI—O—isopropylidene-2-acetylamino-D-mannitol

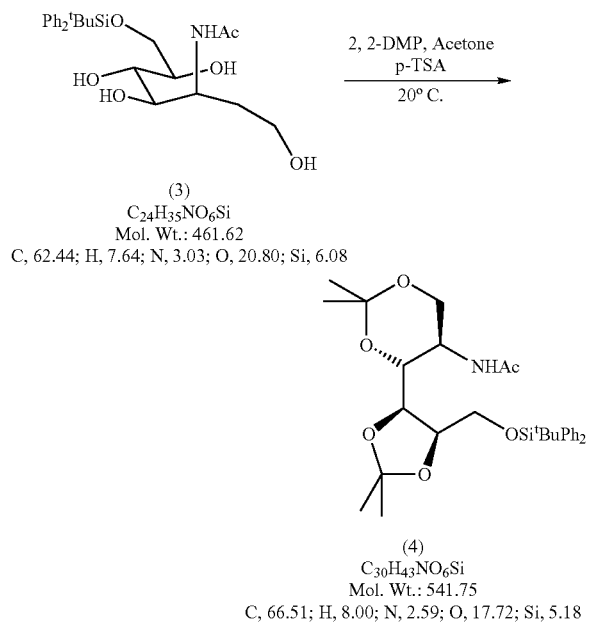

The tetrol (3) (60 g, 0.13 mol) was dissolved in 500 mL of anhydrous acetone and 2,2-dimethoxypropane (123 mL, 1.04 mol) was added followed by 10 mol % para-toluenesulfonic acid monohydrate (2.5 g, 0.013 mol). The mixture was stirred under an inert atmosphere at 20° C. for five hours, at which time the reaction was judged complete by TLC (ethyl acetate). Sodium carbonate was added to the reaction mixture until a neutral suspension was obtained. The suspension was filtered and the solution concentrated under reduced pressure to afford 66 g of a colourless foam. This material was suspended in ethyl acetate (500 mL; warmed to 60° C.) and filtered through a plug of silica. The silica plug was further eluted with ethyl acetate (500 mL). The solvent was removed under reduced pressure to afford a colourless solid (50 g). This material was recrystallised from distilled light petroleum ether (500 mL) to provide (4) (42.5 g, 60%) as a colourless solid. R$_f$ 0.38 (ethyl acetate/petroleum ether, 3:1). Mp 67–69° C. $^1$H NMR (300 MHz, CDCl$_3$) δ: 7.68–7.64 (4H, m), 7.46–7.35 (6H, m), 5.60 (1H, br d, J=8.6 Hz), 4.39–3.59 (8H, m), 1.92 (3H, s), 1.45, 1.34, 1.27, 1.19 (all 3H, s), 1.08 (9H, s). $^{13}$C NMR (300 MHz, CDCl$_3$) δ: 170.1, 136.0, 135.9, 133.8, 133.6, 130.2, 128.2, 128.1, 109.7, 99.6, 76.4, 70.9, 63.3, 63.1, 47.0, 27.3, 26.8, 26.3, 23.8, 21.0, 19.6.

Example 5

Preparation of 2-amino-2-deoxy-1,3:4,5-DI—O—isopropylidene-D-mannitol

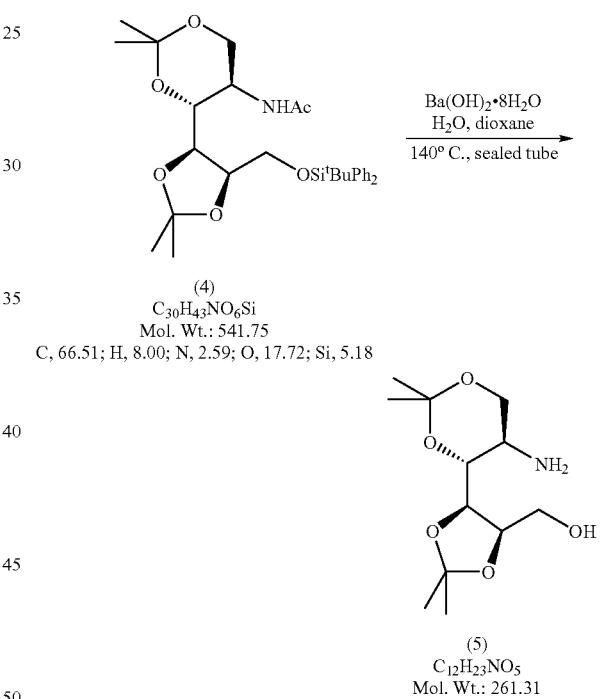

The diacetonide (4) (18 g, 0.033 mol) was dissolved in 60 mL of 1,4-dioxane, at 50° C., in a sealable tube. Water (120 mL) was added followed by barium hydroxide octahydrate (52.4 g, 0.17 mmol), generating a suspension. The tube was sealed and stirred at approx. 140° C. for 15 hours. The mixture was cooled, filtered through Celite and the resulting cake further washed with 1,4-dioxane-water (1:2; 2×40 mL). The filtrate was concentrated under reduced pressure and the resulting grey residue was co-distilled twice with 100 mL volumes of methanol to provide a fine off-white solid. The solid was dissolved in methanol (150 mL) and solid carbon dioxide pellets were added until a neutral pH was obtained. The suspension was concentrated to dryness until approx. 20 mL of suspension remained. Ethyl acetate (100 mL) was added generating a fine solid within a very pale yellow solution. This suspension was heated to 70° C. and the solution decanted off and filtered through Celite. The remaining solid was re-extracted at 70° C. with ethyl acetate/methanol (5:1; 150 mL) and the resulting suspension filtered through Celite. The cake was washed with further ethyl acetate/methanol (5:1; 2×50 mL) and the filtrates were concentrated to dryness to provide a pale yellow oil (approx. 13 g). The oil was subjected to flash chromatography to afford (5) (6.6 g, 80%) as a white solid. $R_f$ 0.18 (ethyl acetate/methanol, 5:1). $^1$H NMR (300 MHz, CDCl$_3$) δ: 4.49 (1H, dd, J=1.6, 6.7 Hz), 4.32–4.26 (1H, m), 3.90–3.72 (3H, m), 3.45–2.51 (2H, m), 3.14–3.06 (1H, m), 2.05–1.83 (2H, br s), 1.52, 1.47, 1.41, 1.38 (each 3H, s). $^{13}$C NMR (300 MHz, CDCl$_3$) δ: 109.1, 99.2, 78.3, 75.0, 74.4, 66.5, 61.6, 46.2, 28.8, 27.0, 26.1, 19.7.

This material has been previously reported (J. Rouden and T. Hudlicky, *J. Chem. Soc. Perkin Trans.* 1, 1095, 1993, J. Rouden, T. Hudlicky, H. Luna and S. Allen, *J. Am. Chem. Soc.*, 116, 5099, 1994) although no data was presented for this compound.

Example 6

Preparation of 2-deoxy-1,3:4,5-DI—O—isopropylidene-2-oxamoylamino-D-mannitol

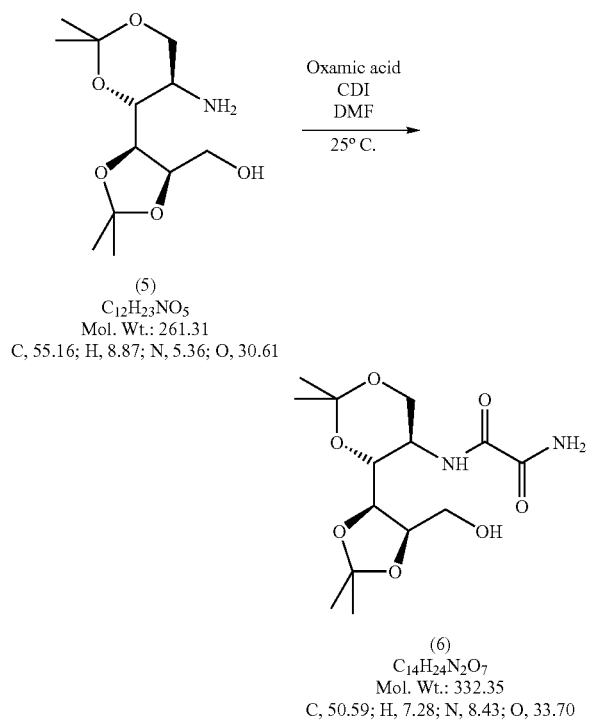

Oxamic acid (1.02 g, 11.5 mmol) was dissolved in 15 mL of anhydrous N,N—dimethylformamide, at 60° C., under an inert atmosphere and the resulting solution cooled to 25° C. In a separate flask, 1,1'-carbonyldiimidazole (CDI) (1.93 g, 11.9 mmol) was dissolved in 15 mL of anhydrous N,N—dimethylformamide, under an inert atmosphere, at 25° C. In another flask, the amino alcohol (5) (2 g, 7.7 mmol) was dissolved in 5 mL of anhydrous N,N—dimethylformamide, under an inert atmosphere, at 25° C. The oxamic acid solution was added dropwise, at 25° C., to the CDI solution over a period of 30 minutes. After stirring for a further 20 minutes at 25° C., the amino alcohol solution was added dropwise over 10 minutes. The reaction mixture was left to stir at 25° C. overnight. Analysis by TLC (9:1, ethyl acetate:methanol) indicated the presence of starting material. A further portion of activated oxamic acid was made from additional solutions of oxamic acid (0.52 g, 5.86 mmol) and CDI (1.0 g, 6.17 mmol) in 5 mL anhydrous N,N—dimethylformamide in an identical fashion to that above. The solution of additional activated oxamic acid is then added dropwise over 15 minutes to the original reaction mixture and stirring continued at 25° C. for 1 hour. Analysis by TLC indicated complete consumption of starting material. Water (1 mL) was added to the reaction mixture with continued stirring for 30 minutes. The resulting mixture was then concentrated under reduced pressure and the residue subjected to dry-flash chromatography to provide (6) (2.04 g, 80%) as a white solid. This material has been previously reported (H. Kayakiri, C. Kasahara, K. Nakamura, T. Oku, and M. Hashimoto, *Chem. Pharm. Bull.*, 39, 1392, 1991) and data obtained corresponded to that observed in the literature.

Example 7

Preparation of 2-deoxy-1,3:4,5-DI—O—isopropylidene-2-oxamoylamino-D-mannitol

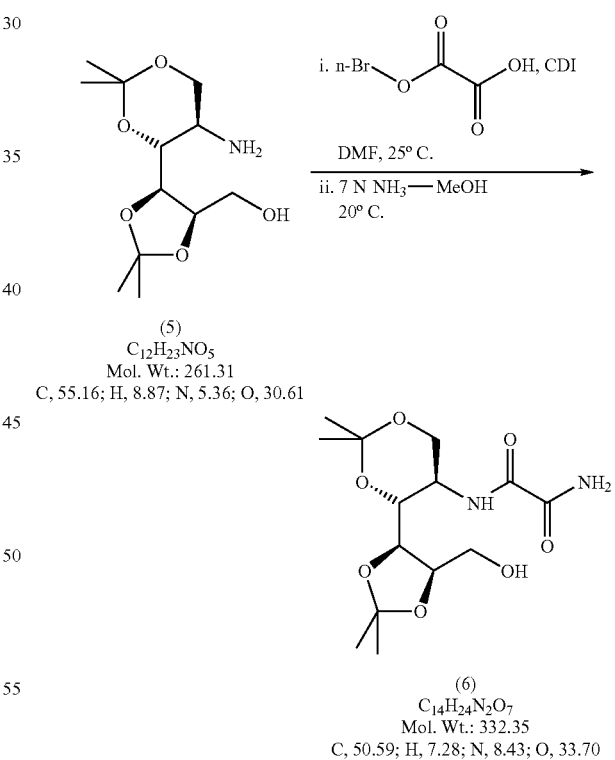

Oxalic acid mono-n-butyl ester (0.84 g, 5.75 mmol) was dissolved in 5 mL of anhydrous N,N—dimethylformamide under an inert atmosphere, at 25° C. In a separate flask, 1,1'-carbonyldiimidazole (CDI) (0.93 g, 5.75 mmol) was dissolved in 5 mL of anhydrous N,N—dimethylformamide, under an inert atmosphere, at 25° C. In another flask, the amino alcohol (5) (1 g, 3.8 mmol) was dissolved in 5 mL of anhydrous N,N—dimethylformamide, under an inert atmosphere, at 25° C. The oxalic acid mono-n-butyl ester solution was added dropwise, at 25° C., to the CDI solution over a period of 15 minutes. After stirring for a further 20 minutes at 25° C., the amino alcohol solution was added dropwise over 10 minutes. The reaction mixture was left to stir at 25° C. overnight. Analysis by TLC (9:1, ethyl acetate:methanol) indicated the presence of starting material. A further portion of activated oxalic acid mono-n-butyl ester was made from additional solutions of oxalic acid mono-n-butyl ester (0.14 g, 0.96 mmol) and CDI (0.16 g, 0.96 mmol) in 2 mL of anhydrous N,N—dimethylformamide in an identical fashion to that above. The solution of additional activated oxalic acid mono-n-butyl ester is then added dropwise over 15 minutes to the original reaction mixture and stirring continued at 25° C. for 2 hours. Analysis by TLC indicated complete consumption of starting material. Water (1 mL) was added to the reaction mixture with continued stirring for 30 minutes. The resulting mixture wass then partitioned between 100 mL of water and 50 mL of ethyl acetate. The aqueous layer is then extracted twice more with 50 mL portions of ethyl acetate. The organic layers were combined and washed successively with 25 mL of 2M hydrochloric acid, 25 mL of water and 50 mL of saturated, aqueous sodium bicarbonate solution. The ethyl acetate layer was then dried over magnesium sulfate, filtered and the filtrate was concentrated under reduced pressure generating a colourless oil (1.60 g). The oil was dissolved in 25 mL of approx. 7 N methanolic ammonia and the resulting suspension (the formation of a white precipitate is immediately observed) was sealed and stirred for 16 h at 20° C. The suspension was filtered through Celite and the cake washed with methanol (2×10 mL). The solvents were concentrated under reduced pressure to afford the product as a pale yellow oil (approx. 1.30 g). The oil was subjected to flash chromatography to afford (6) (0.92 g, 73%) as a white solid. This material has been previously reported (H. Kayakiri, C. Kasahara, K. Nakamura, T. Oku, and M. Hashimoto, *Chem. Pharm. Bull.*, 39, 1392, 1991) and data obtained corresponded to that observed in the literature.

Example 8

Preparation of 2-deoxy-1,3:4,5-DI—O—isopropylidene-2-oxamoylamino-D-mannitol

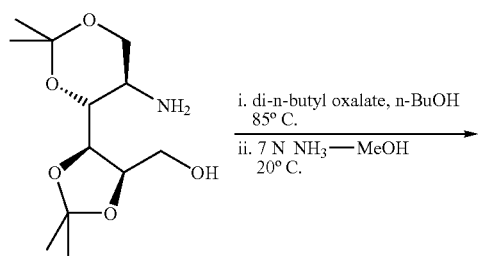

(5)
$C_{12}H_{23}NO_5$
Mol. Wt.: 261.31
C, 55.16; H, 8.87; N, 5.36; O, 30.61 i. di-n-butyl oxalate, n-BuOH
85° C.

ii. 7 N NH₃—MeOH
20° C.

-continued

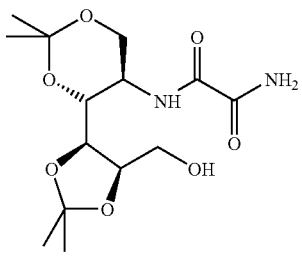

(6)
$C_{14}H_{24}N_2O_7$
Mol. Wt.: 332.35
C, 50.59; H, 7.28; N, 8.43; O, 33.70 di-n-Butyl oxalate (261 mg, 1.29 mmol) was dissolved in 3 mL of n-butanol, under an inert atmosphere, at 25° C. The amino alcohol (5) (225 mg, 0.86 mmol) was added as a single portion and the resulting solution was heated to 85° C. and agitated for 16 hours. The solvent was removed under reduced pressure to provide a colourless oil. The oil was then partitioned between ethyl acetate (15 mL) and water (5 mL) and the organic layer further extracted with water (2×5 mL). The organic layer was dried over magnesium sulfate, filtered and the solvent removed under reduced pressure affording a colourless residue (261 mg). The residue was dissolved in 10 mL of approx. 7 N methanolic ammonia and the resulting suspension (the formation of a white precipitate is immediately observed) was sealed and stirred for 16 h at 20° C. The suspension was filtered through and the cake washed with methanol (2×10 mL). The solvents were concentrated under reduced pressure and the resulting residue was co-distilled twice with dichloromethane (2×10 mL) to afford (6) as a white solid (140 mg, 49%). This material has been previously reported (H. Kayakiri, C. Kasahara, K. Nakamura, T. Oku, and M. Hashimoto, *Chem. Pharm. Bull.*, 39, 1392, 1991) and data obtained corresponded to that observed in the literature.

Example 9

Preparation of 5-deoxy-2,3:4,6-DI—O—isopropylidene-2-oxamoylamino-D-mannose

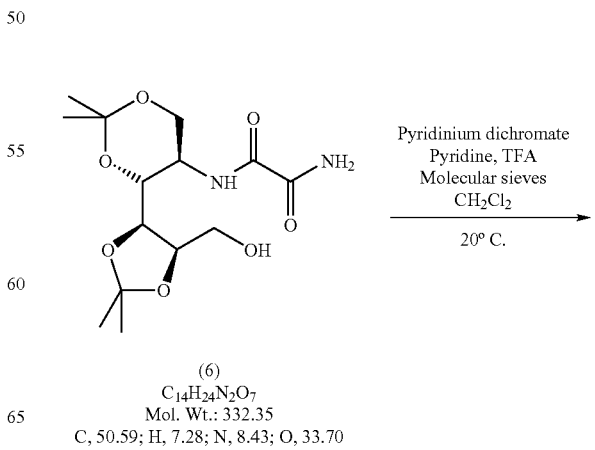

(6)
$C_{14}H_{24}N_2O_7$
Mol. Wt.: 332.35
C, 50.59; H, 7.28; N, 8.43; O, 33.70

Pyridinium dichromate
Pyridine, TFA
Molecular sieves
$CH_2Cl_2$

20° C.

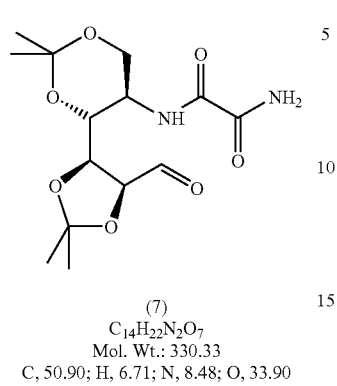

(7)
C$_{14}$H$_{22}$N$_2$O$_7$
Mol. Wt.: 330.33
C, 50.90; H, 6.71; N, 8.48; O, 33.90

The oxamoylated alcohol (6) (0.50 g, 1.50 mmol), in anhydrous dichloromethane (5 mL), was added to activated 4 Å molecular sieves (0.5 g) and the mixture was stirred at 20° C., under an inert atmosphere, for 15 minutes. Pyridinium dichromate (0.56 g, 1.50 mmol), pyridine (anhydrous, 125 μL) and trifluoroacetic acid (TFA, 100 μL) were added rapidly to the mixture, dropwise, in quick succession. The dark brown mixture was stirred at room temperature under an inert atmosphere for 30 minutes.

The mixture was poured into 20 mL of ethyl acetate and passed through a plug of silica, eluting with 5×30 mL volumes of ethyl acetate. The filtrates were concentrated under reduced pressure providing crude (7) as a brown oil (0.50 g). This material has been previously reported (H. Kayakiri, C. Kasahara, K. Nakamura, T. Oku, and M. Hashimoto, *Chem. Pharm. Bull.*, 39, 1392, 1991) and data obtained corresponded to that observed in the literature.

Example 10

Preparation of 2,3:4,6-DI—O—isopropylidene-kifunensine

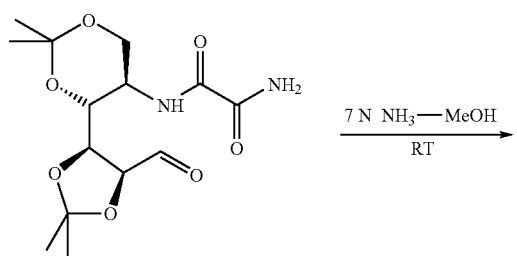

(7)
C$_{14}$H$_{22}$N$_2$O$_7$
Mol. Wt.: 330.33
C, 50.90; H, 6.71; N, 8.48; O, 33.90

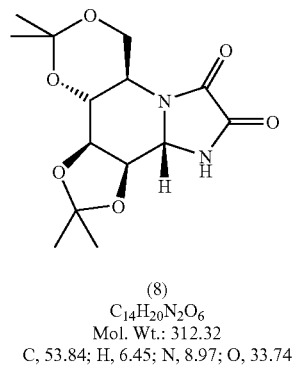

(8)
C$_{14}$H$_{20}$N$_2$O$_6$
Mol. Wt.: 312.32
C, 53.84; H, 6.45; N, 8.97; O, 33.74

The crude aldehyde (7) (0.50 g) was dissolved in 10 mL of approx. 7 N methanolic ammonia and the resulting solution sealed and stirred overnight at RT. The mixture was concentrated to dryness and the residue was co-distilled twice with 15 mL volumes of methanol. The resulting brown residue, crude (8), (approx. 320 mg) was used directly in the final step. This material has been previously reported (H. Kayakiri, C. Kasahara, K. Nakamura, T. Oku, and M. Hashimoto, *Chem. Pharm. Bull.*, 39, 1392, 1991) and data obtained from purified (8) (via chromatography) corresponded to that observed in the literature.

Example 11

Preparation of Kifunensine

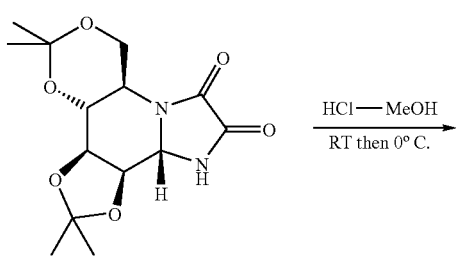

(8)
C$_{14}$H$_{20}$N$_2$O$_6$
Mol. Wt.: 312.32
C, 53.84; H, 6.45; N, 8.97; O, 33.74

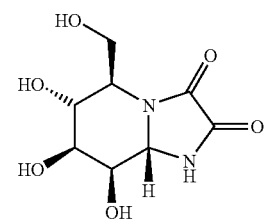

Kifunensine
C$_8$H$_{12}$N$_2$O$_6$
Mol. Wt.: 232.19
C, 41.38; H, 5.21; N, 12.06; O, 41.34

The cyclised species (8) was dissolved in 3 mL of methanol and cooled to approx. 5° C. Concentrated hydrochloric acid (1.5 mL) was added dropwise over 5 minutes and the mixture stirred at RT for 30 minutes. An off-white precipitate was observed. The suspension was chilled in an ice-water bath for 30 minutes, filtered and the resulting cake washed with chilled methanol (2×5 mL) to provide crude Kifimensine, obtained as an off-white solid (121 mg). Purified Kifinensine (102 mg, 28% yield based on oxamoylated alcohol substrate) is obtained after a single recrystallisation from water (2 mL). This material has been previously reported (H. Kayakiri, S. Takase, T. Shibata, M. Hashimoto, T. Toda and S. Koda, Chem. Pharm. Bull., 39, 1378, 1991, H. Kayakiri, C. Kasahara, K. Nakamura, T. Oku, and M. Hashimoto, Chem. Pharm. Bull., 39, 1392, 1991) and data obtained corresponded to that observed in the literature.

Although the invention has been described by way of example, it should be appreciated that variations or modifications may be made without departing from the scope of the claims. Furthermore, when known equivalents exist to specific features, such equivalents are incorporated as if specifically referred to in the specification.

What is claimed is:

1. A process for preparing a compound of formula (I), or a salt thereof:

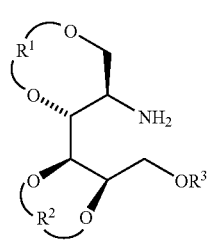

(I)

where $R^1$ and $R^2$ are each independently protecting groups which, together with the oxygen atoms to which they are attached, form part of a dioxane or dioxolane ring; and $R^3$ is hydrogen or a protecting group;
including the steps of:
(a) protecting the hydroxyl group at the C-6 position of N—acetyl-D-mannosamine, to give a 6—O—protected—N—acetyl-D-mannosamine, wherein the hydroxyl protecting group at the C-6 position is selected from the group consisting of a silyl group, a benzyl group, or an ester group;
(b) reducing the C-1 anomeric carbon atom of the 6—O—protected—N—acetyl-D-mannosamine using a reducing agent selected from the group consisting of a metal hydride reducing agent or hydrogen gas/metal catalyst to give a 6—O—protected —N—acetyl-D-mannitol;
(c) protecting the four hydroxyl groups of the 6—O—protected—N—acetyl-D-mannitol with protecting groups $R^1$ and $R^2$ as defined above;
(d) removing the N—acetyl protecting group using basic conditions and optionally removing the C-6 oxygen atom protecting group using basic conditions to give the compound of formula (I).

2. A process according to claim 1 where 2,2-dimethoxypropane in the presence of acetone is used to protect the four hydroxyl groups of the 6—O—protected—N—acetyl-D-mannitol in step (c), to give a 1:3, 4:5-di—O—isopropylidene-D-mannitol.

3. A process according to claim 1 where both the N—acetyl protecting group and the C-6 oxygen atom protecting group are removed in step (d).

4. A process according to claim 1 further comprising:
(e) oxamoylation of the compound of formula (I) to give a 2-oxamoylamino-D-manmtol;
(f) removal of the $R^3$ protecting group using basic conditions, where $R^3$ is not H;
(g) oxidation of the C-6 carbon atom to give a 2-oxamoylamino-D-mannose;
(h) double cyclisation of the 2-oxamoylamino-D-mannose using a methanolic ammonia solution to give kifunensine with four protected hydroxyl groups; and
(i) removal of the four hydroxyl protecting groups using acidic conditions to give kifunensine.

5. A process according to claim 3 where oxamic acid and 1,1'-carbonyldiimidazole are used for the oxamoylation of the compound of formula (I) in step (e).

6. A process according to claim 3 where the oxamoylation step (e) is a direct coupling of the compound of formula (I) with ethyl oxamate, oxalic acid mono-n-butyl ester or di-n-butyl oxalate.

7. A process according to claim 3 where pyridinium dichromate in the presence of activated molecular sieves and pyridinium trifluoroacetate is used for the oxidation of the C-6 carbon atom in step (g).

8. A process for preparing kifunensine including the steps of:
(a) silylation of N—acetyl-D-mannosamine using tert-butyldiphenylsilyl chloride as silylating agent, to give 6—O—tert-butyldiphenylsilyl-2-deoxy-2-acetylamino-D-mannose;
(b) reduction of 6—O—tert-butyldiphenylsilyl-2-deoxy-2-acetylamino-D-mannose using sodium borohydride as reducing agent, to give 6—O—tert-butyldiphenylsilyl -2-deoxy-2-acetylamino-D-marmitol;
(c) protection of the four hydroxy groups of 6—O—tert-butyldiphenylsilyl-2-deoxy-2-acetylamino -D-mannitol using 2,2-dimethoxypropane in the presence of acetone, to give 6—O—tert-butyldiphenylsilyl-2-deoxy- 1,3:4,5 -di—O—isopropylidene -2-acetylamino-D-mannitol;
(d) double deprotection of the 6—O— and N—protecting groups of 6—O—tert-butyldiphenylsilyl -2-deoxy-1,3 :4,5-di—O—isopropylidene-2-acetylamino-D-mannitol using aqueous barium hydroxide, to give 2-amino-2-deoxy-1,3:4,5-di —O—isopropylidene-D-mannitol;
(e) oxamoylation of 2-amino-2-deoxy- 1,3 :4,5-di—O—isopropylidene-D-mannitol using oxamic acid and 1,1'-carbonyidjimidazole, to give 2-deoxy- 1,3 :4,5-di—O—isopropylidene -2-oxamoylamino-D-mannitol;
(f) oxidation of 2-deoxy- 1,3 :4,5-di—O—isopropylidene-2-oxamoylamino-D-mannitol using pyridinium dichromate in the presence of activated molecular sieves and pyridinium trifluoroacetate, to give 5-deoxy-2,3:4,6-di—O—isopropylidene -5-oxamoylamino-D-mannose;
(g) double cyclisation of 5-deoxy-2,3:4,6-di—O—isopropylidene-5-oxamoylamino-D-mannose using a methanolic ammonia solution, to give 2,3:4,6-di—O—isopropylidene -kifunensine; and
(h) deprotection of 2,3:4,6-di—O—isopropylidene-kifunensine, using methanolic hydrochloric acid, to give kifunensme.

9. A process according to claim 1 where the hydroxyl protecting group at the C-6 position of N—acetyl-D-mannosamine in step (a) is a silyl protecting group.

10. A process according to 9 where the silyl protecting group is tert-butyldiphenylsilyl.

11. A process according to claim 1 where the basic conditions in step (d) are selected from aqueous barium hydroxide or sodium n-butoxide in n-butanol.

12. A process according to claim 4 where the basic conditions in step (f) are selected from aqueous barium hydroxide or sodium n-butoxide in n-butanol.

13. A process according to claim 4 where the acidic conditions in step (i) are selected from methanolic hydrochloric acid or trifluoroacetic acid.

14. A process according to claim 1 further comprising:
   (e) removal of the $R^3$ protecting group using basic conditions, where $R^3$ is not H;
   (f) oxamoylation of the compound of formula (I) to give a 2-oxamoylamino-D-mannitol;
   (g) oxidation of the C-6 carbon atom to give a 2-oxamoylamino-D-mannose;
   (h) double cyclisation of the 2-oxamoylamino-D-mannose using a methanolic ammonia solution to give kifunensine with four protected hydroxyl groups; and
   (i) removal of the four hydroxyl protecting groups using acidic conditions to give kifunensine.

15. A process according to claim 4, wherein $R^3$ is a silyl group or an ester group.

16. A process according to claim 14, wherein $R^3$ is a silyl group or an ester group.

* * * * *